United States Patent [19]

Kao et al.

[11] Patent Number: 5,288,870
[45] Date of Patent: Feb. 22, 1994

[54] SYNTHESIS OF SPECIFICALLY LABELED TETRODOTOXIN

[75] Inventors: Chien-yuan Kao, Pound Ridge; Biqi Wu, Brooklyn, both of N.Y.

[73] Assignee: Research Foundation of the State University of New York, Albany, N.Y.

[21] Appl. No.: 793,597

[22] Filed: Nov. 18, 1991

[51] Int. Cl.$^5$ .............................. C07D 491/052
[52] U.S. Cl. .............................. 544/247; 544/330
[58] Field of Search .............................. 544/247, 330

[56] References Cited

PUBLICATIONS

Yang et al. Toxicon, 30 (5/6), 645–652, 1992.
Yang et al. J. Gen Physiol, 100, 609–622, 1992.
Lee et al. Can. J. of Chemistry, 43, 2924–2927 1965.
Wilzbach: Journal of Amer. Chem. Soc. 79:1013 (1957).
Mosher: Annals of The New York Acad. of Sci. 479:32–43 (1986).
Levinson: Philosophical Trans. Royal Soc. of London (Ser. B) 270: 337–348 (1975).
Grunhagen et al: Archives of Biochem. and Biophys. 206:198–204 (1981).
Kovalenko et al: Bioorganic Khimi 8:710–712 (1982).
Chicherportiche et al: European J. of Biochem. 104:617–625 (1980).
Khora et al: Tetrahedron Letters. 30:349–350 (1989).

*Primary Examiner*—Mukund J. Shah
*Assistant Examiner*—Y. N. Gupta
*Attorney, Agent, or Firm*—Morgan & Finnegan

[57] ABSTRACT

The present invention relates to a process for the preparation of specifically labelled TTX of high specific activity. In the present process, TTX is oxidized by use of the Pfitzer-Moffat method or Fenton's reagent and the aldehyde obtained is hydrated. The hydrated aldehyde is reduced with alkali metal o alkaline earth metal borotritide. The radioactive TTX so obtained, quite surprisingly, has a specific activity many times greater than previously prepared radioactive TTX.

13 Claims, 3 Drawing Sheets

SYNTHESIS OF SPECIFICALLY LABELED TETRODOTOXIN

Tetrodotoxin (TTX) and saxitoxin (STX) are important neurobiological tools because of their selective and high-affinity blockade of the voltage-gated sodium channel of many excitable membranes. As such, they have not only sided in the isolation of the sodium channel macromolecule, but are also potentially useful in further structural clarifiation of the channel protein. Although their sources and chemical structures are quite different, their biological actions are virtually identical in that they share the unique channel specificity and a channel affinity measured in equilibrium dissociation constants of nanomolar concentrations. The similarities of their actions imply the presence of similarities in chemical structures which are involved in their interactions with the sodium channel. More specifically, a better understanding of their interactions with the channel protein could serve as a landmark for orientation in additional structural clarification of the sodium channel protein.

The structure of TTX has been determined and is given by the following formula:

Until recently, few studies of the structure-activity relations of either TTX or STX have been successful. In the case of TTX, most derivatives made during chemical studies of its structure in the early 1960s were too extensively modified to be of much revelatory value. In the case of STX, questions about its structure were not resolved until it was successfully crystallized in 1975. The separatory and detection technologies for both toxins were such that contamination with minute amounts of the highly potent toxins themselves could not be excluded with certainty, rendering suspect some observations on the weaker analogues.

For lack of specific information, explanations of how TTX and STX blocked the sodium channel were based largely on unproven assumptions.

The availability of a suitably labeled form of an agent is crucial to studies of the action of many physiologically active substances. Most such studies with labeled TTX itself have made use of material tritiated by the Welzbach method (exposing TTX to tritium gas) (Wilzbach, K. E. 1957, J. Am. Chem. Soc. 79: 1013-1015). There is extensive degradation of TTX in this process and its purification has required exacting methods, accompanied by large losses (Levinson, S. R. 1975, Philos. Trans. R. Soc. London 270: 337-348. Balerna, M., M. Fosset, R. Chicheportiche, G. Romey and M. Lazdunsky, 1975). The ultimate recovery of pure [$^3$H]TTX is low (ca. 1%), and its radioactivity not particularly high (ca. 100–400 Ci/mol).

A process involving hydrolysis of anhydro TTX with tritium oxide in order to obtain tritiated TTX (0.7% chemical yield, 18,000 Ci/mole) has been reported recently (Grunhagen, H. H., M. Rack, R. Stampfli, H. Fasold & P. Reiter, 1981, Arch. Biochem. Biophys 206: 198-204). The product is claimed to have 60% of the radioactivity expected for the incorporation of one $^3$H atom per molecule of TTX. It was proposed that the reaction involves epimerization at the anhydro bridge with $^3$H incorporation at C-4. However, specific evidence for this was not presented.

In spite of this proposal, the chemical rationale for tritium incorporation is unclear.

An alternate approach to the tritiation problem is the incorporation of radioactivity into a reagent, which is then attached to the TTX structure.

None of the prior compounds are readily available. Although they have been used to isolate the sodium channel, they are unsuitable for more detailed studies of the peptide structure of the binding site for at least two reasons:

(a) The ethylene diamine coupled TTX derivatives are too large to be binding unequivocally only to the TTX/STX binding site. Because of the probable size and shape of that binding site, it is doubtful that the label could be on the binding site.

(b) The specific activities of the tritium-labelled toxins are too low, and they also suffer from exchange diffusion with solvent protons during the experiment. Another deficiency concerns the reliability of the nature of the product, such as the ethylene diamine coupled derivatives. The first step used in the synthesis of those compounds was an oxidation of TTX to a reactive derivative, which was then used for further synthesis. However, the nature of the oxidation product is completely unknown. Nothing was ever isolated or characterized and all claims were based on theoretical expectations of anticipated reactions.

It is an object of the present invention to provide a new method for producing a stable, specifically labelled radioactive TTX of high-specific activity. It is a still further object of the present invention to provide a labelled TTX derivative in which the radioactive moiety is attached to the TTX molecule.

SUMMARY OF THE INVENTION

The present invention relates to a process for the preparation of specifically labelled TTX of high specific activity. In the present process, TTX is oxidized by use of the Pfitzer-Moffat method or Fenton's reagent and the aldehyde obtained is hydrated. The hydrated aldehyde is reduced with alkali metal or alkaline earth metal borotritide. The radioactive TTX so obtained, quite surprisingly, has a specific activity many times greater than previously prepared radioactive TTX.

Using the present process, 11-oxo TTX was prepared by oxidation of commercially available TTX. Possible oxidation reactions include oxidation with hydrogen peroxide and iron sulfate (Fenton's reagent) or oxidation with dimethylsulfoxide and dicyclohexylcarbodiimide (DCCI)(Pfitzner-Moffat oxidation). Oxidation takes place at the hydroxymethyl group of TTX to the aldehyde. The aldehyde then reacts with any water present in the reaction medium to form the aldehyde hydrate of TTX. Because it is nearly impossible to conduct the oxidation reaction in a completely anhydrous environment, the aldehyde hydrate is normally obtained.

The 11-oxo TTX is then reduced back to radioactive TTX using a radioactive alkali metal or alkaline earth metal borotritide, e.g. with sodium borotritide. Tritium labelled TTX is obtained in overall good yield compared with prior procedures and with a surprisingly high specific activity.

The 11-oxo TTX prepared in the present process was characterized by comparison with an authentic sample of 11-oxo TTX by chromatography and NMR and proved to be the same material.

The yield of 11-oxo TTX which can be obtained ranges up to about 20% and higher. In TTX chemistry, such yields are considered to be highly encouraging.

The product of the instant process when sodium borotritide is used as the reducing agent is $^3$HTTX specifically labelled at one of the methylene hydrogens of the hydroxymethylene group. Because of the high cost and health hazards of the highly radioactive tritide used in the present process, preliminary work was done using the non-radioactive hydride. Although the overall yield for the entire process (14%) is not as high as expected, it is still about six times better than the prior art. Additionally, the product of the instant process needs very little or no clean up work.

When radioactive borotritide is used, the yield of radioactive TTX is low, the overall yield from TTX to labelled TTX being 6.4%. The reason for the low yield, as compared with that in the non-radioactive reaction, is that the radioactive borotritide was present in large excess. The amount of tritide could not be controlled too well, because the radioactive reagent came in too small a quantity to be weighed. Also, it was not possible to dilute the radioactive reagent in acetic acid before the reaction, because the tritium label in the reagent would be lost in the procedure. Hence, the reaction was carried out by a crude estimate of stochiometry of TTX to the radioactive borotritide. If the reaction were scaled up to a point where the radioactive borotritide can be weighed beforehand, it should be possible to achieve a yield closer to that obtained for the non-radioactive reaction.

DETAILED DESCRIPTION OF THE INVENTION

Figure 1:
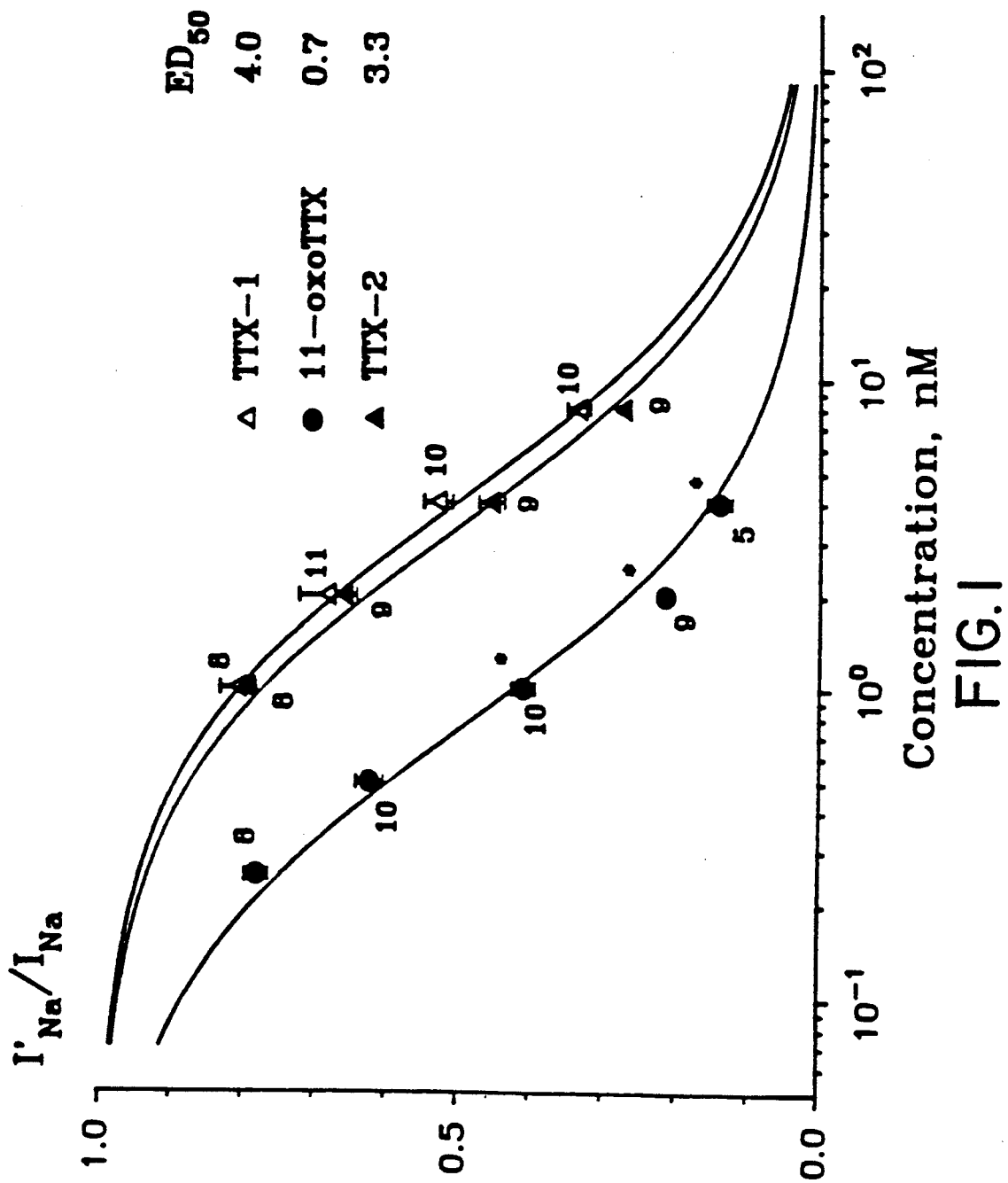
FIG. 1 is a plot of blockage of sodium channels against log toxin concentration.
Figure 2:
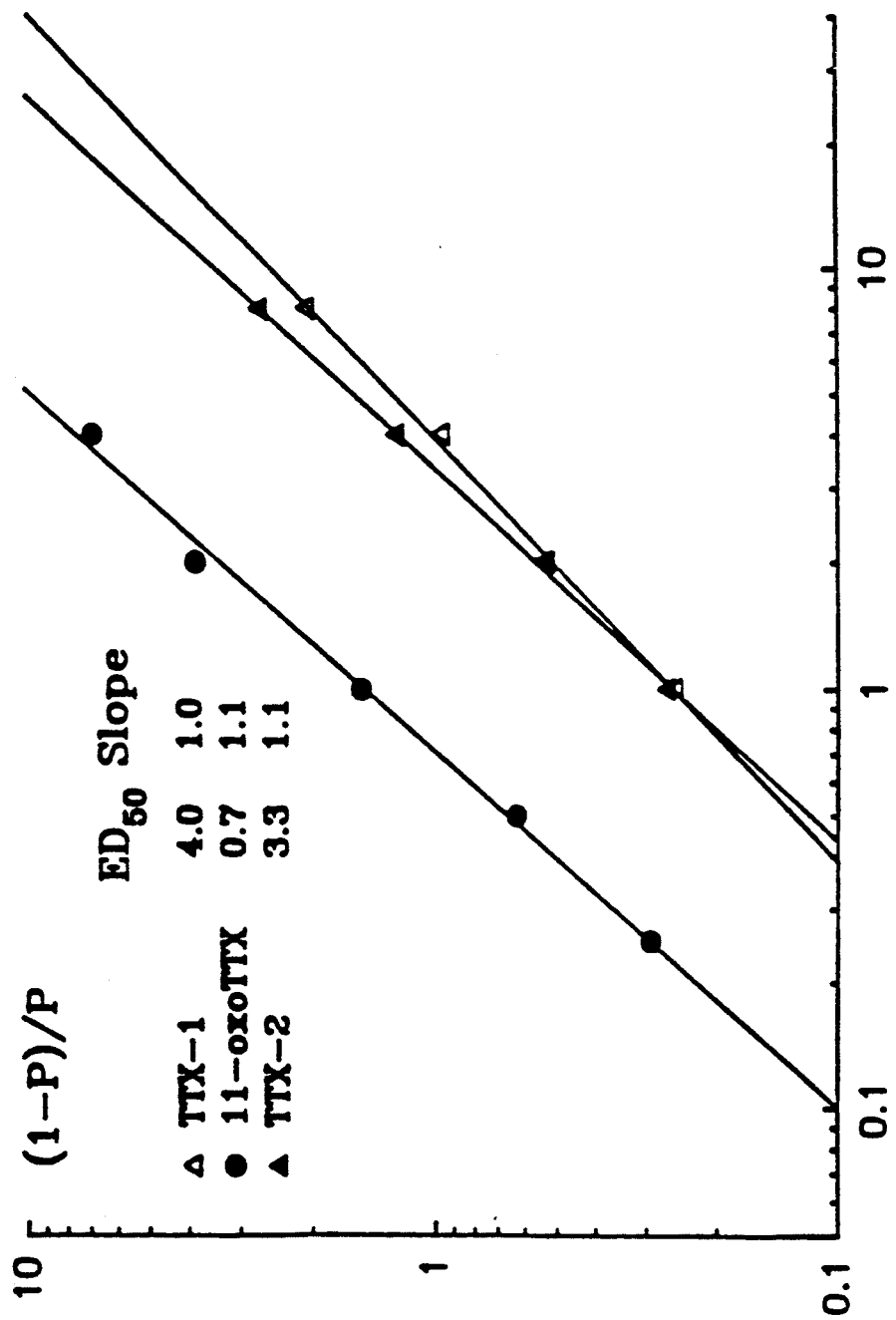
FIG. 2 is a Hill plot of data in FIG. 1 showing 1 toxin molecule blocked 1 sodium channel.
Figure 3:
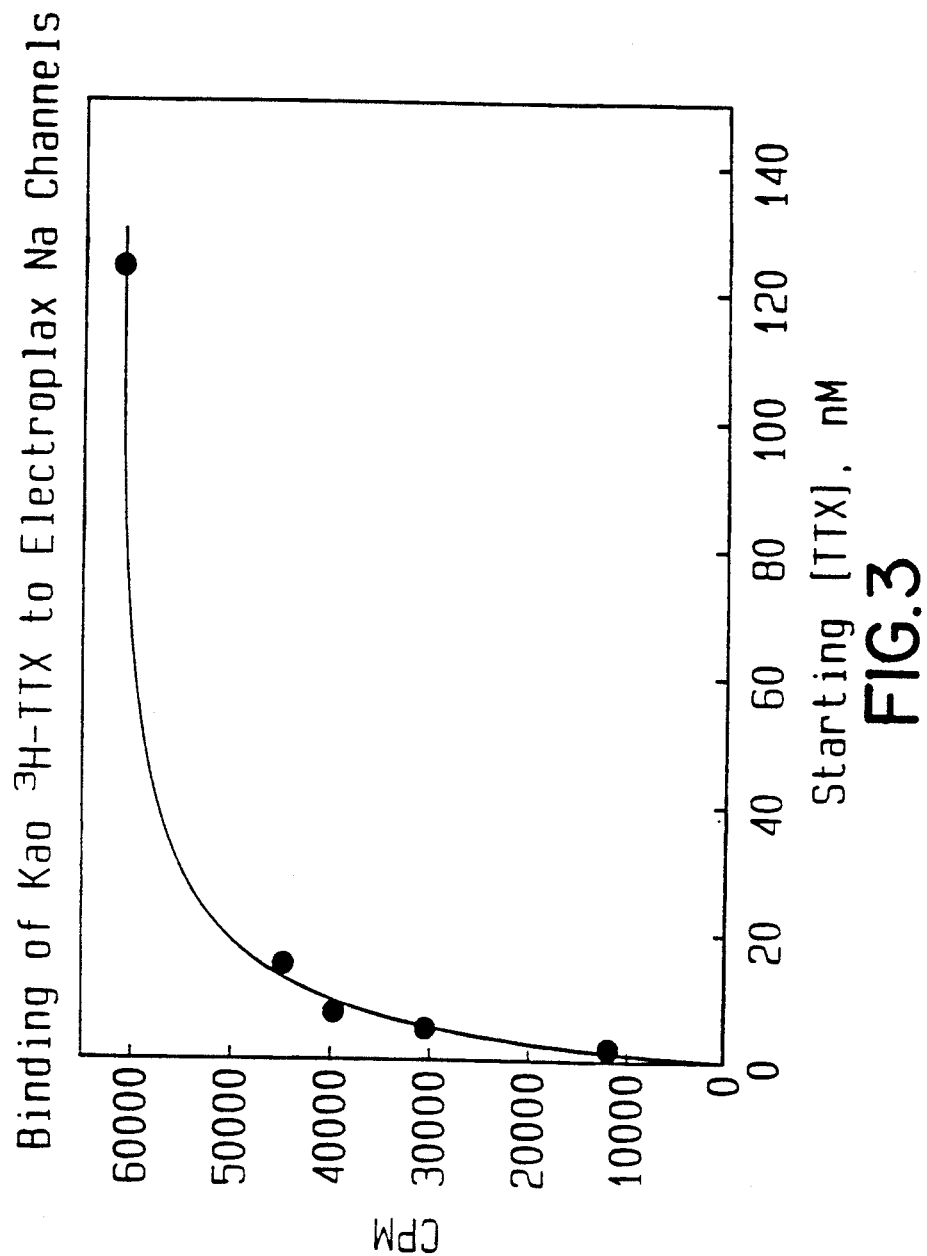
FIG. 3 shows the specific binding of our $^3$HTTX to electroplax Na channels.

I. Experimental Details of Making Specifically Radioactive Labelled Tetrodotoxin A. Oxidation of TTX to 11-oxo-TTX with Fenton's reagent 30% hydrogen peroxide ($H_2O_2$, 200 µl) and ferrous sulfate ($FeSO_4$ $7H_2O$: 2 µmol, 560 µg) in 7 µl of $H_2O$ were added to a solution of TTX (4 mg, 0.0125 mM) in 0.5M acetic acid (HOAc, 100 ul). The reaction mixture was kept at 25° C. for 2.4 hr and then brought to pH 6–7 by addition of 2.5–2.8% ammonium hydroxide ($NH_4OH$, ca. 50 µl). The neutralized reaction mixture was chromatographed on a Bio Rex 70 column (400 mesh, 1×5 cm) equilibrated with water. The column was washed with water (40 ml), and 11-oxoTTX, TTX and its derivatives were eluted with 0.05 M HOAc (flow rate 0.96 ml/min). The eluates were monitored by use of a TTX-analyzer.

The fractions containing 11-oxo TTX, TTX and its derivatives were combined and concentrated to about 400 ul. The concentrated fraction was loaded on a Shodex ODS pack column (0.46×25 cm) with a buffered ion-pairing solution (20 mM sodium heptanesulfonate, 5 mM $H_3PO_4$, and adjusted to pH 7.2 with $NH_4OH$). This column separated the structurally close analogues of TTX. The fractions containing 11-oxoTTX, as detected with the TTX analyzer, were combined and concentrated to approximately 400 ul. The concentrate was loaded on a Hitachi gel 3013C column (0.46×15 cm) equilibrated with water, for desalting. The column was washed with water (22.4 ml) and then 0.05M HOAc (flow rate 0.8 m./min). The fractions containing 11-oxoTTX, detected in the TTX analyzer, were combined, concentrated, and lypholized, giving 450 ug of 11-oxo TTX (yield of about 10.2%).

B. Oxidation of TTX to 11-oxoTTX by the Pfitzner-Moffat reaction

This reaction was carried out under anhydrous conditions. All of the reagents were carefully dried. Dimethyl sulfoxide (DMSO), orthophosphoric acid ($H_3PO_4$), and dicyclohexyl carbodiimide (DCCI) were dried over 0.3 nm molecular sieves for 2 weeks, and stored in a dessicator.

TTX (4.26 mg, 13.3 µM) was dissolved in 0.5% trifluroacetic acid ($CF_3COOH$, 200 µl) in a 1 ml reaction vial and lypholized in the vial. A magnetic bar was added to the reaction vial, and the entire complex was kept in a dessicator overnight. The microsyringes used in the reaction were also dried in the same dessicator.

To the dried TTX were added 0.5M DCCI/DMSO (208.8 µl, 104 µM) and 1M $H_3PO_4$ (6.26 µl, 6.26 µM). The resulting reaction mixture was stirred at room temperature (ca. 22° C.) in a strictly sealed vial. After 5.5 hrs, 150 µl of water was added to the reaction mixture, and the entire contents were then centrifuged. The supernatant was filtered through a small pipette packed with a small amount of cotton. The residue (N,N'-dicyclohexylurea) was twice washed with water (100 µl). The combined filtrate was injected into a Shodex ODS-5 column which had been equilibrated with a buffered solution of 20 mM sodium 1-heptasulfonate, 5 mM $H_3PO_4$ and $NH_4OH$ (pH 7.2. flow rate 0.8 ml/min. fraction=0.8 min). The fractions containing 11-oxoTTX, as detected with a TTX analyzer, were evaporated in vacuo to 400 μl, which was then charged onto a Hitachi gel 3013C column equilibrated with water (flow rate 0.8 ml/min, fraction=2 min). After 28 min, 0.05N HOAc was introduced for the elution of 11-oxoTTX.

11-oxoTTX (907 μg, yield 20.3%) with a purity of 96.0% was obtained, based on HPLC analysis compared with an authentic sample of the compound. $^1H$ NMR spectrum, shown in Table 1 is identical with that published.

C. Reduction of 11-oxoTTx to TTX (non=radioactive)

To a solution of 11-oxoTTX (279.5 μg, 0.832 μM) in 97.6 ml of 92.%5 HOAc was added sodium borohydride ($NaBH_4$, 184.0 μg in 10 μl HOAc) at 10° C. The reaction was stopped after 20 min by addition of 5 ml of water. The reaction mixture was concentrated in vacuo to about 350 μl, and the concentrate then charged onto a Hitachi gel 3013C column (0.46×15 cm). The column was washed with water (28 ml, flow rate 1 ml/min) and then with 0.05M HOAc. The eluates were monitored in the TTX analyzer. The fractions containing TTX were combined, concentrated and lypholized, giving 229.9 μg of TTX (yield 86.4%). In another run, the yield was 55.4%. The mean yield of the two runs is 70.9%. The structure of TTX was confirmed by $^1H$ NMR (see Table 1, below). The overall yield of the reaction TTX→11-oxoTTX→TTX is 14.2%.

D. Reduction of 11-oxoTTX to $^3$HTTX

A solution of 11-oxoTTX (308.9 ug, 0.919 uM) in 92.5% HOAc (142.8 μl) was added dropwise to a suspension of tritiated sodium borohydride ($^3HNaBH_4$, 100 mCi, 549 ug, 14.4 uM) in acetonitrile, (30 ul) at 5°-10° C. After 25 min, the reaction was stopped by addition of 1 ml of water. The reaction mixture was removed to a 10 ml flask with 4 ml water. The solution was evaporated in vacuo to about 450 μl, which was then chromatographed on Hitachi gel 3013C column (mobil phase, $H_2O$, 28 min, 0.05N HOAc, flow rate 1 ml/min, fraction=2 min) to give the labelled TTX (92.3 μg, yield 31.4%). The chemical purity of the labelled TTX was 88.2%, based on HPLC analysis. The specific radioactivity was 2900 Ci/mol.

TABLE 1.

1H NMR spectra of TTX, 11-oxoTTX and regenerated TTX.

| C | 11-oxoTTX | Regenerated TTX | Original TTX | Corrected* |
|---|---|---|---|---|
| 4 | 5.46 (d 9.5) | 5.60 (d 9.6) | 5.47 (d 8.8) | 5.60 |
| 4a | 2.27 (d 9.4) | 2.46 (d 9.6) | 2.33 (d 9.2) | 2.46 |
| 5 | 4.33 (br s) | 4.41 (br s) | 4.28 (br s) | 4.41 |
| 7 | 4.15 (br s) | 4.19 (br s) | 4.06 (br s) | 4.19 |
| 8 | 4.23 (br s) | 4.36 (br s) | 4.23 (br s) | 4.36 |
| 9 | 3.93 (s) | 4.06 (s) | 3.93 (s) | 4.06 |
| 11 | 5.70 (s) | 4.14 (d 8) | 4.01 (d 11) | 4.14 |

Right column shows carbon atom number to which proton is attached. Data are in ppm in $D_2O$ and $CD_3COOD$ from an internal standard of residual $CH_3COOH$. In parenthesis, type of signal and coupling constant; d=doublet; br s=broad singlet, s=singlet. Spectra of original TTX was taken on a different occasion; difference from regenerated TTX is due to some slight downfield shift of the entire spectra, as readily proven by correction of adding 0.13 ppm to all signals.

The $^3$HTXX obtained in the present process has a specific activity of about 3,000 Ci/mol. An important advantage of the present $^3$HTXX is its stability. In the present $^3$HTTX, the tritium label is in a position where it does not exchange with solvent protons.

The regenerated TTX (non-radioactive) has been tested electrophysiologically, and found to have identical effects and potencies as its original TTX. The $^3$HTTX has been tested in binding studies to isolated sodium channel, and found to bind specifically to the TTX-receptor, but giving a signal at least 60 times better than the currently available diffusely labelled TTX.

E. Electrophysiological Testing

Single muscle fibers were dissected from the semitendinosus muscle of the English frog, *Rana temporaria*, and placed in a vaseline-gap voltage-clamp apparatus for determining the sodium and potassium currents produced by depolarization. The effects of TTX and 11-oxoTTX are mainly on the sodium current ($I_{Na}$).

The potencies of the toxins were determined as dose-response relations in which response is the residual sodium current ($I_{Na}'$). The dose-response relations are plotted as $I_{Na}'/I_{Na}$ (ordinate) vs log concentration of toxin (in nanomols) (FIG. 1).

In Hill plots where response as log (1-P)/P(P=I'-Na/$^1$Na) is plotted against log toxin concentration, the $ED_{50}$ (effective dose for 50% reduction of $I_{Na}$) can be read when (1-P)/P=1. The slope of the curves (close to 1.0) shows that the toxin-receptor interaction occurs without any cooperactivity, i.e., one molecule of toxin blocks one sodium channel (FIG. 2).

The $ED_{50}$ for the original TTX (TTX-1, 4.0 nM) and that for the regenerated TTX (TTX-2, 3.3 nM) are not statistically significant (Student's t-test, p>0.3). The $ED_{50}$ of 11-oxoTTX (0.7 nM) is significantly lower than that of TTX, i.e., 11-oxoTTX is more potent in blocking the sodium channel than is TTX.

Binding Assay on Purified Sodium Channel of Electric Eel

This assay was performed by an expert on isolated sodium channel and an acknowledged authority on the diffusely labelled TTX. The material used was purified from the electric eel, *Electrophorus electricus.*

The curve shows a saturable binding, i.e., specific binding to the TTX receptor, at a radioactivity some 60 times higher than is attainable with a diffusely labelled TTX (FIG. 3).

I we claim:

1. A process for the preparation of labeled tetrodotoxin having high specific activity comprising the steps of:

a) oxidizing tetrodotoxin to 11-oxo-tetrodotoxin;

b) hydrating the 11-oxo-tetrodotoxin;

c) reducing the hydrated 11-oxo-tetrodotoxin with an alkali metal or alkaline earth metal tritide.

2. A process according to claim 1, wherein the oxidation is done using the Pfitzer-Moffat method.

3. A process according to claim 1, wherein the oxidation is done using Fenton's reagent.

4. A process according to claim 1, wherein the reduction is carried out with sodium borotritide.

5. A process according to claim 1, wherein hydration step b) occurs during oxidation step a) by reaction with water present in the oxidation reaction medium.

6. Labeled tetrodotoxin obtained by the process according to claim 1.

7. Labeled tetrodotoxin prepared by the process according to claim 2.

8. Labeled tetrodotoxin prepared by the process according to claim 3.

9. Labeled tetrodotoxin prepared by the process according to claim 4.

10. Labelled tetrodotoxin according to claim 6, wherein the high specific activity is at least 60 times better than the activity of currently available diffusely labelled tetrodotoxin.

11. Labelled tetrodotoxin according to claim 7, wherein the high specific activity is at least 60 times better than the activity of currently available diffusely labelled tetrodotoxin.

12. Labelled tetrodotoxin according to claim 8, wherein the high specific activity is at least 60 times better than the activity of currently available diffusely labelled tetrodotoxin.

13. Labelled tetrodotoxin according to claim 9, wherein the high specific activity is at least 60 times better than the activity of currently available diffusely labelled tetrodotoxin.

* * * * *